US012657831B2

(12) United States Patent
Massarwa et al.

(10) Patent No.: US 12,657,831 B2
(45) Date of Patent: Jun. 16, 2026

(54) CORRECTING A SEGMENTATION CURVE IN AN ANATOMICAL MODEL

(71) Applicant: BIOSENSE WEBSTER (ISRAEL) LTD., Yokneam (IL)

(72) Inventors: Fady Massarwa, Baka al Gharbiyya (IL); Shir Kolangi Yosub, Yokneam Ilit (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 246 days.

(21) Appl. No.: 18/216,021

(22) Filed: Jun. 29, 2023

(65) Prior Publication Data

US 2024/0020926 A1     Jan. 18, 2024

Related U.S. Application Data

(60) Provisional application No. 63/389,217, filed on Jul. 14, 2022.

(51) Int. Cl.
| | |
|---|---|
| *A61B 34/10* | (2016.01) |
| *G06T 7/11* | (2017.01) |
| *G06T 17/20* | (2006.01) |

(52) U.S. Cl.
CPC ............ *G06T 17/205* (2013.01); *A61B 34/10* (2016.02); *G06T 7/11* (2017.01); *A61B 2034/105* (2016.02);
(Continued)

(58) Field of Classification Search
CPC .................... G06T 17/205; G06T 7/11; G06T 2207/30048; G06T 7/12; G06T 19/20;
(Continued)

(56) References Cited

U.S. PATENT DOCUMENTS

| | | | |
|---|---|---|---|
| 5,391,199 A | 2/1995 | Ben-Haim | |
| 5,443,489 A | 8/1995 | Ben-Haim | |

(Continued)

FOREIGN PATENT DOCUMENTS

| | | | |
|---|---|---|---|
| EP | 3441944 A1 | 2/2019 | |
| EP | 3961564 A1 | 3/2022 | |

OTHER PUBLICATIONS

Watanabe, Yoshiaki. "A Method for Estimating the Centroid of an Organ Based on Double Integrals on Serial Cross Sections." IEEE transactions on biomedical engineering 1 (1986): 60-63. (Year: 1986).*

(Continued)

*Primary Examiner* — Kent W Chang
*Assistant Examiner* — Karl Duc Truong
(74) *Attorney, Agent, or Firm* — Smith, Gambrell & Russell LLP

(57)     ABSTRACT

A system includes a display and a processor. The processor obtains a three-dimensional mesh representing a first anatomical portion and a second anatomical portion, which is connected to the first anatomical portion. The processor receives, from a user, an input indicating a boundary between the first and second anatomical portions, fits a closed curve to multiple points on the mesh based on the input, and performs an iterative process, in response to the curve not segmenting the mesh into two separate parts, until the curve segments the mesh into two separate parts. Each iteration includes moving each of the points to another location on the mesh, and subsequently to moving each point, refitting the curve to the points. The processor is further configured to display the mesh on the display, based on the curve, so as to demarcate the first anatomical portion from the second anatomical portion.

26 Claims, 5 Drawing Sheets

(52) U.S. Cl.
    CPC ................... *A61B 2034/107* (2016.02); *G06T*
                      *2207/30048* (2013.01)

(58) Field of Classification Search
    CPC . G06T 2207/20096; G06T 2207/20101; A61B
               34/10; A61B 2034/105; A61B 2034/107
    See application file for complete search history.

(56) References Cited

U.S. PATENT DOCUMENTS

| | | | |
|---|---|---|---|
| 5,558,091 | A | 9/1996 | Acker et al. |
| 6,172,499 | B1 | 1/2001 | Ashe |
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 6,788,967 | B2 | 9/2004 | Ben-Haim et al. |
| 6,892,091 | B1 | 5/2005 | Ben-Haim et al. |
| 7,536,218 | B2 | 5/2009 | Govari et al. |
| 7,756,576 | B2 | 7/2010 | Levin |
| 7,848,787 | B2 | 12/2010 | Osadchy |
| 7,869,865 | B2 | 1/2011 | Govari et al. |
| 8,456,182 | B2 | 6/2013 | Bar-Tal et al. |
| 2010/0189320 | A1* | 7/2010 | Dewaele ................... G06T 7/11 |
| | | | 382/128 |
| 2014/0330111 | A1* | 11/2014 | Lichtenstein ............ A61B 5/02 |
| | | | 600/508 |
| 2015/0049081 | A1* | 2/2015 | Coffey ................... A61B 34/10 |
| | | | 345/419 |
| 2015/0049082 | A1* | 2/2015 | Coffey ................. G06T 7/0012 |
| | | | 345/420 |
| 2017/0213338 | A1* | 7/2017 | Groth ........................ G06T 7/12 |
| 2018/0122150 | A1* | 5/2018 | Bidne .................... G06T 17/00 |
| 2018/0137626 | A1* | 5/2018 | Lawrenson ............. G06F 18/41 |
| 2018/0158252 | A1* | 6/2018 | Stehle .................... A61B 6/466 |
| 2018/0225884 | A1* | 8/2018 | Yamada .................. G06T 7/149 |
| 2018/0330506 | A1* | 11/2018 | Grady ..................... G06T 7/174 |
| 2021/0201493 | A1* | 7/2021 | Auerbach .............. G16H 30/40 |
| 2022/0254104 | A1* | 8/2022 | Zhang ..................... G06T 17/20 |
| 2023/0011809 | A1* | 1/2023 | Groth ........................ G06F 3/14 |

OTHER PUBLICATIONS

Kang, Dongwoo, et al. "Heart chambers and whole heart segmentation techniques." Journal of Electronic Imaging 21.1 (2012): 010901-010901. (Year: 2012).*

FalcÃ£o, Alexandre X., Jayaram K. Udupa, and Flavio Keidi Miyazawa. "An ultra-fast user-steered image segmentation paradigm: live wire on the fly." IEEE transactions on medical imaging 19.1 (2000): 55-62. (Year: 2000).*

Ecabert, Olivier, et al. "Automatic model-based segmentation of the heart in CT images." IEEE transactions on medical imaging 27.9 (2008): 1189-1201. (Year: 2008).*

International Search Report for corresponding PCT Appln. No. PCT/IB2023/057145 dated Oct. 23, 2023.

Lee y et al: "Mesh scissoring with minima rule and part salience", Computer Aided Geometric Design, North-Holland, Amsterdam, NL, vol. 22, No. 5, Jul. 1, 2005.

Funkhouser Thomas et al:"Modeling by example", ACM Transactions on Graphics, ACM, NY, US, vol. 23, No. 3, Aug. 1, 2004 (Aug. 1, 2004) , pp. 652-663.

Zheng Yefeng et al: "Multi-Part Modeling and Segmentation of Left Atrium in C-Arm CT for Image-Guided Ablation of Atrial Fibrillation", IEEE Transactions on Medical Imaging, IEEE, USA, vol. 33, No. 2, Feb. 1, 2014.

* cited by examiner

CORRECTING A SEGMENTATION CURVE IN AN ANATOMICAL MODEL

CROSS-REFERENCE TO RELATED APPLICATION

This application claims the benefit of U.S. Provisional Patent Application 63/389,217, filed Jul. 14, 2022, which is incorporated herein by reference.

FIELD OF THE DISCLOSURE

The present disclosure is related generally to the field of anatomical modeling, and specifically to segmentation of a model.

BACKGROUND

An image of an anatomical organ may be generated from a mesh of the organ. In the image it is useful to delineate sections of the image by segmentation, i.e., by marking boundaries on the image separating the sections.

BRIEF DESCRIPTION OF THE DRAWINGS

The present disclosure will be more fully understood from the following detailed description of examples thereof, taken together with the drawings, in which.

DETAILED DESCRIPTION OF EXAMPLES

Overview

Figure 1:
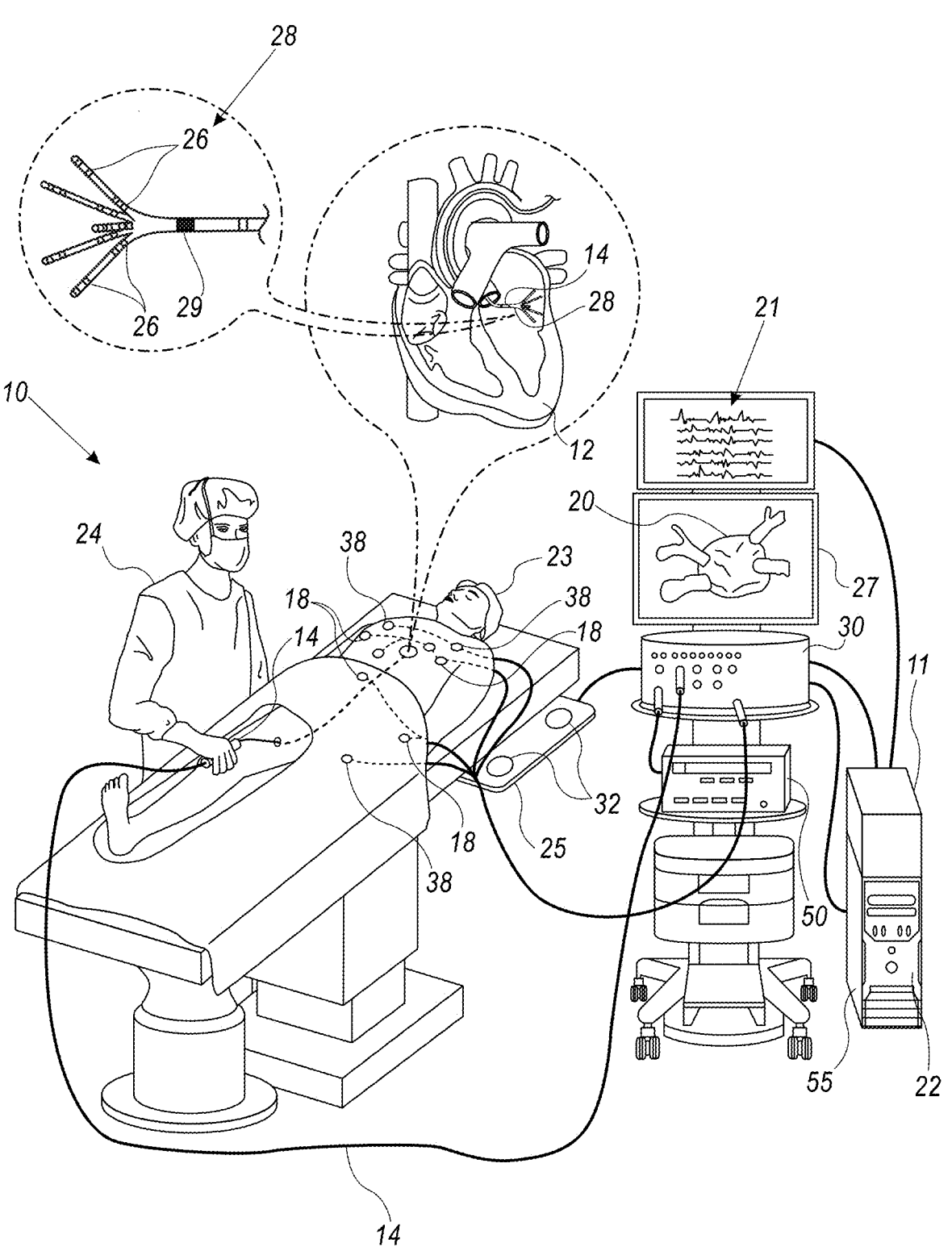
FIG. 1 shows a catheter-based electrophysiology mapping and ablation system, according to an example of the present disclosure.

In an electrophysiology mapping procedure, a digital map of a region of a heart may be acquired as a mesh of points on the surface of one or more chambers of the heart. For any given chamber, once the mesh has been acquired, a physician may segment the mesh to show elements of the chamber, and/or elements attached to the chamber. The segmentation comprises delineating boundaries of the different elements. For example, for the left atrium (LA), the physician may want to show the boundaries of the left atrium appendage (LAA), and of the four pulmonary veins (PVs), to the LA. It will be understood that each boundary is a closed segmentation curve that separates elements on either side of the boundary.

Examples of the present disclosure assist the physician in implementing the segmentation of the mesh, by providing the physician with a tool enabling the physician to mark a small number of points on the mesh, at locations assumed by the physician to correspond to points on a desired boundary. A processor then calculates a curve, for instance a B-spline curve, connecting each pair of neighboring marked points. Each section of the curve connecting neighboring marked points is herein termed a link of the curve.

The processor evaluates each link of the curve by projecting sample points from the link onto their closest location on the mesh, and measuring the distances between neighboring projected points. For a given link, providing the measured distances are close enough to each other, i.e., within some preset threshold distance, the processor assumes the calculated link is valid, so that it is usable. If all the links of the curve are found to be valid, then the curve forms a closed segmentation curve, and this closed curve is assumed to be the desired boundary.

However, if one of the links of the curve is invalid, so that it is unusable, then the remaining links of the curve do not form a closed curve, but rather an open curve, and this open curve cannot operate as a boundary.

The open curve terminates in two marked disconnected points, and the processor may use the following algorithm to close the open curve.

The processor computes the shortest geodesic path on the mesh between the projections of the two disconnected points, and adds an additional point at the middle of the path. The processor then calculates a new curve, using the additional point and the marked points, and evaluates the new curve. The processor performs this process iteratively until convergence, i.e., until a closed curve is formed.

In some cases, even when a closed curve is formed, the closed curve does not act as a boundary between elements. Such a case occurs when the mesh contains a topological hole, and the closed curve passes through the hole. The processor may identify this type of problem by, after generating the closed curve, selecting an element of the mesh, herein by way of example assumed to be a triangle in a triangular mesh, on one side of the closed curve. The processor then registers neighboring triangles of the mesh contacting the selected triangle, and iteratively continues the registration until all possible neighboring triangles have been registered.

If the registered triangles are only a subset of the triangles of the whole mesh, then the closed curve is a boundary between disjoint elements of the mesh.

However, if the registered triangles consist of all the triangles of the mesh, then the closed curve is not a boundary between disjoint elements. In this case the processor iteratively moves the points used to generate the closed curve by a predefined distance, normal to the curve, and checks if the closed curve is a boundary. The iterative point movement may initially be distal, away from the center of the mesh. If after a preset number of distal iterations the closed curve is not a boundary, the iterations of the points may then be performed proximally, towards the mesh center.

DETAILED DESCRIPTION

In the following description, like elements are identified by the same numeral, and are differentiated, where required, by having a letter attached as a suffix to the numeral.

Reference is now made to FIG. 1 which shows a catheter-based electrophysiology mapping and ablation system 10, according to an example of the present disclosure. System 10 includes multiple catheters, which are percutaneously inserted by a physician 24 through the patient's vascular system into a chamber or vascular structure of a heart 12. Typically, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals and/or mapping heart 12, catheters dedicated for ablating and/or catheters dedicated for both sensing and/or mapping and ablating. An example catheter 14 that is configured for sensing and mapping is illustrated herein. Physician 24 brings a distal tip 28 of catheter 14 into contact with the heart wall for sensing electropotentials (EPs) at a target site in heart 12, as well as for mapping one or more chambers of the heart.

Catheter 14 is an exemplary multi-spine catheter that includes multiple electrodes 26 distributed on the spines of the catheter. Catheter 14 may additionally include a position sensor 29 embedded in or near distal tip 28 for tracking the position and orientation of distal tip 28. Optionally and preferably, position sensor 29 is a magnetic based position sensor including three magnetic coils for sensing three-dimensional (3D) position and orientation.

Magnetic based position sensor 29 may be operated together with a location pad 25 including a plurality of magnetic coils 32 configured to generate magnetic fields in a predefined working volume. The real time position of distal tip 28 of catheter 14 may be tracked based on magnetic fields generated with location pad 25 and sensed by magnetic based position sensor 29. Details of the magnetic based position sensing technology are described in U.S. Pat. Nos. 5,391,199; 5,443,489; 5,558,091; 6,172,499; 6,239,724; 6,332,089; 6,484,118; 6,618,612; 6,690,963; 6,788,967; 6,892,091.

System 10 includes one or more electrode patches 38 positioned for skin contact on a patient 23 to establish a location reference for location pad 25 as well as impedance-based tracking of at least some electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848,787; 7,869,865; and 8,456,182.

A recorder 11 displays electrograms 21 captured with body surface ECG electrodes 18 and intracardiac electrograms (IEGM) that may be captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes 26. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, a power supply and a workstation for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, a processor 22 with memory or storage with appropriate operating software loaded therein, and user interface capability. Workstation 55 may provide multiple functions, optionally including (1) modeling the endocardial anatomy in three-dimensions (3D) and rendering a model or anatomical map 20 of all or part of heart 12 for display on a display device 27, typically by first mapping points of a selected portion of the heart, forming a mesh of the points, then covering the mesh with a surface, (2) displaying on display device 27 activation sequences (or other data) compiled from recorded electrograms 21 in representative visual indicia or imagery superimposed on the rendered anatomical map 20, (3) displaying real-time location and orientation of distal tip 28 within the heart chamber, and (4) displaying on display device 27 sites of interest such as places where ablation energy has been applied. One commercial product embodying elements of the system 10 is available as the CARTO™ 3 System, available from Biosense Webster, Inc., 31A Technology Drive, Irvine, CA 92618.

In general, processor 22 may be embodied as a single processor, or as a cooperatively networked or clustered set of processors. The functionality of the processor may be implemented solely in hardware, e.g., using one or more fixed-function or general-purpose integrated circuits, Application-Specific Integrated Circuits (ASICs), and/or Field-Programmable Gate Arrays (FPGAs). Alternatively, this functionality may be implemented at least partly in software. For example, the processor may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

In examples of the disclosure, the physician desires to segment a mapped portion of a chamber of heart 12, using a mesh of the chamber. In the following description, by way of example the chamber to be segmented is assumed to be the left atrium (LA) of heart 12, but those having ordinary skill in the art will be able to adapt the description, mutatis mutandis, for other chambers or parts of the heart, as well as for other organs or parts of organs of patient 23, and all such adaptations are assumed to be comprised within the scope of the present disclosure.

Figures 2A, 2B:
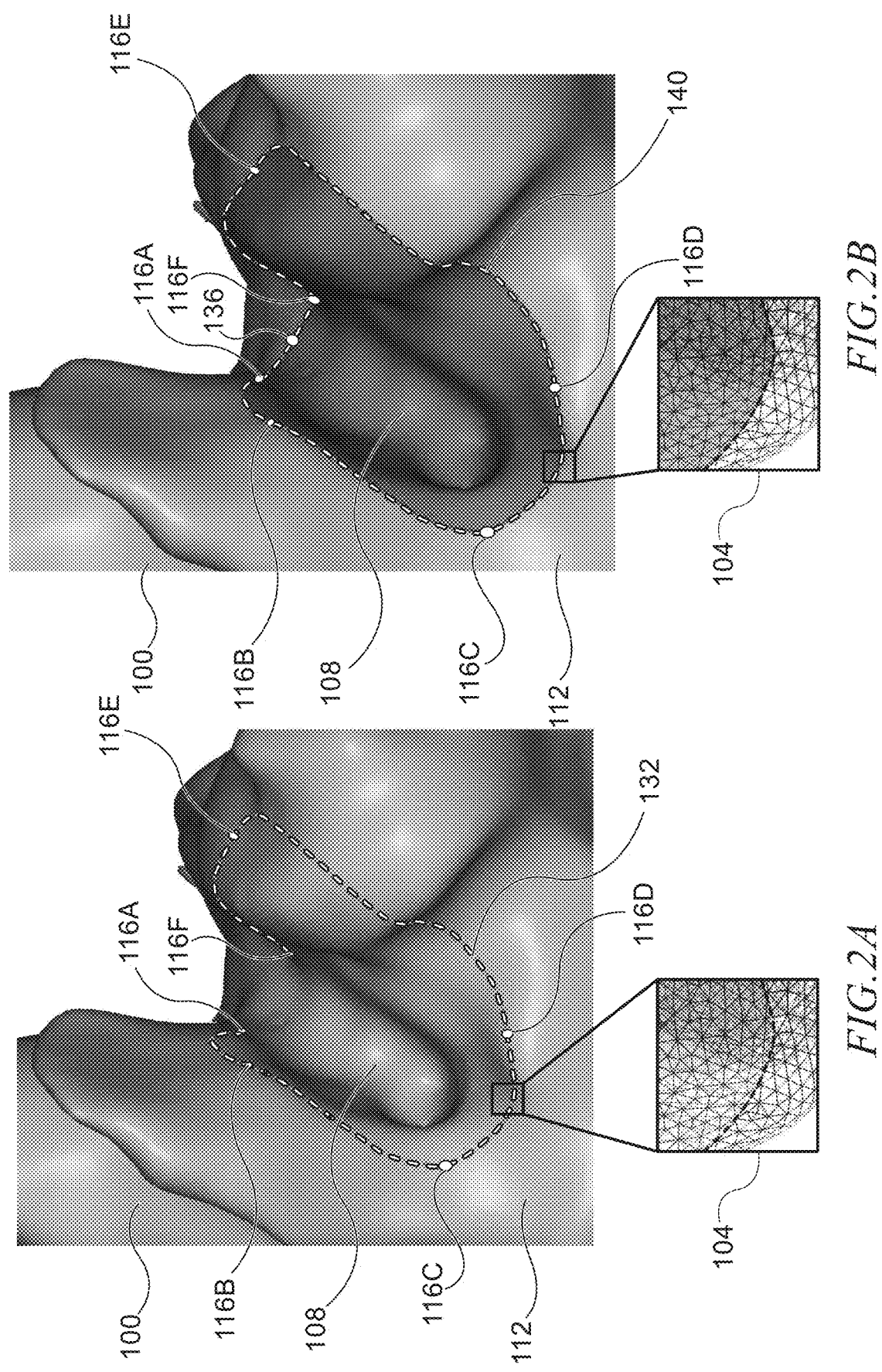
FIGS. 2A and 2B are schematic illustrations of a section of a surface of a left atrium of a heart, according to an example of the present disclosure.
Figure 3:
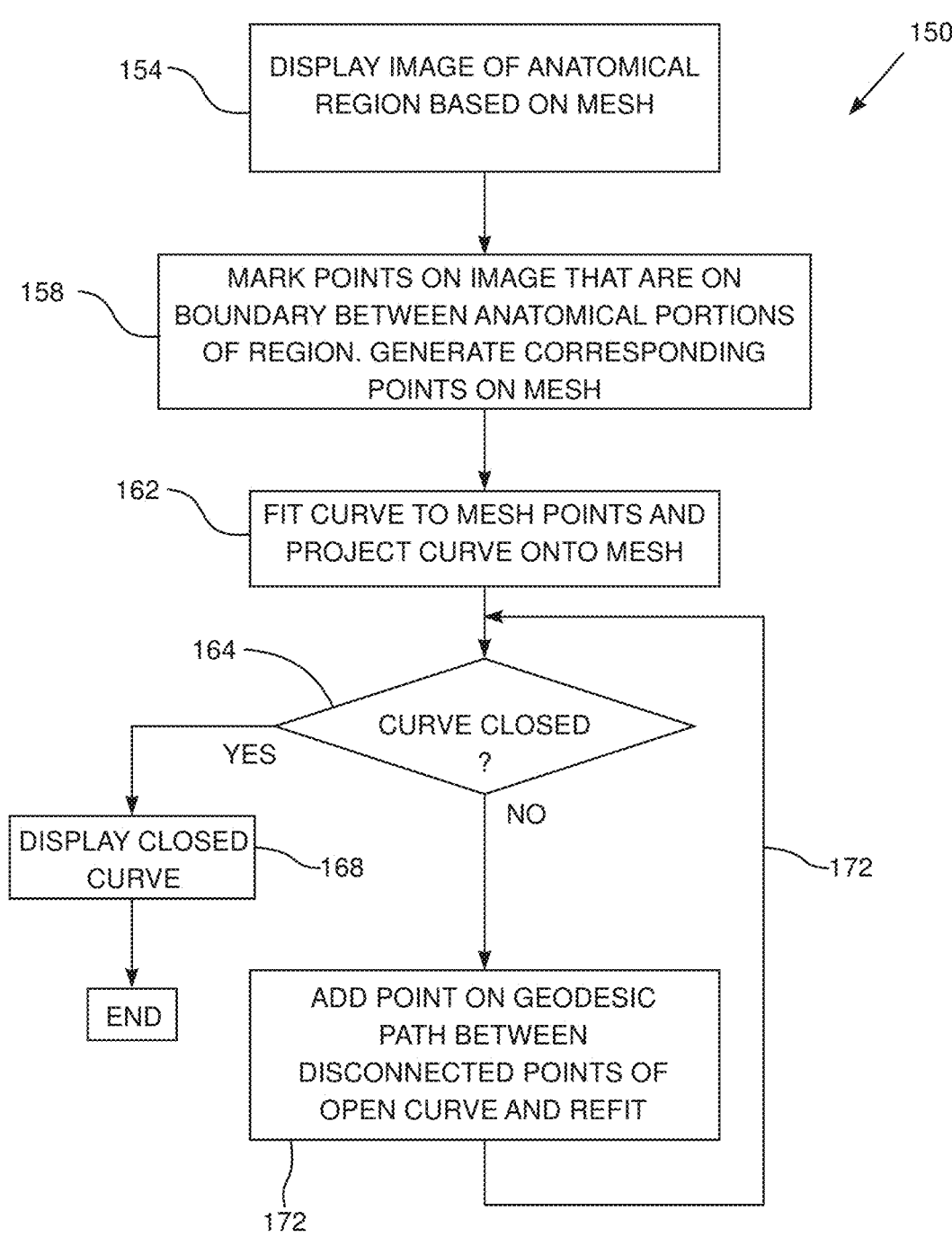
FIG. 3 is a flowchart of steps that are implemented to segment the left atrium, according to an example of the present disclosure.

FIGS. 2A and 2B are schematic illustrations of a section of a surface 100 of the LA of heart 12, as it may be presented to physician 24 on device 27, and FIG. 3 is a flowchart 150 of steps that are implemented to segment the LA, according to an example of the present disclosure. Surface 100 is generated from an underlying triangular mesh 104 of the LA, illustrated in the call-outs of the figures. The illustrations are of a first anatomical portion 108, assumed to comprise a portion of a pulmonary vein, that is connected to a second anatomical portion 112, assumed to comprise the left atrium itself.

In an initial step 154 of the flowchart, processor 22 presents an image of surface 100 to physician 24 on display device 27. As stated above, the processor generates surface 100 from an underlying three-dimensional (3D) triangular mesh 104, and the mesh itself may be obtained by the processor computing mapping measurements made on the left atrium by physician 24, as described above, or by any other convenient method.

In a user input step 158, physician 24 marks a plurality of points on surface 100 that are assumed to be on a boundary dividing anatomical portion 108 from anatomical portion 112. The marking may be implemented, for example, by the physician using a pointing device or by touching the screen of device 27, if so enabled. By way of example, six points are assumed to be marked. Processor 22 registers the locations of the marked points, and uses the registered locations to identify corresponding points 116A, 116B, . . . 116E, 116F, on mesh 104.

In a curve fitting step 162 the processor fits a curve, such as a B-spline curve, connecting the mesh points identified in step 158. The processor then samples points on the curve and projects the sampled points onto their closest locations on mesh 104.

The processor measures the distances between neighboring projected points, and checks that the distances are smaller than a predefined threshold distance. In one example the predefined threshold distance is five times the mean length of the edges of the triangles of mesh 104, but in other examples the predefined threshold distance is larger or smaller than five times the mean length.

If all the distances are smaller than the predefined threshold distance, then the curve generated in step 162, comprising connections, herein also termed links, between points identified in step 158, is assumed to be a valid closed curve. Such a closed curve may be used as a boundary curve segmenting anatomical portion 108 from anatomical portion 112.

There may be a case, typically if the geometry of mesh 104 is complicated, where a measured distance exceeds the predefined threshold distance. In such a case, the processor identifies the link between the corresponding points identified in step 158, and assumes that this link invalidates the closing of the projected curve, so that the corresponding identified points are disconnected, leaving an open curve. Such an open curve cannot be used as a segmentation curve.

FIG. 2A illustrates an open curve 132, where the processor has calculated that a section of the curve calculated in step 162, between disconnected points 116A and 116F, is invalid.

In a decision step 164, the processor checks if step 162 has resulted in a closed curve. If the decision is positive, then in a presentation step 168 the closed curve is incorporated into surface 100 and displayed on device 27, and the flowchart ends.

If the decision in step 164 is negative, then in a recomputing step 172 the processor computes the shortest geodesic path on mesh 104 between the disconnected points identified in step 162, and adds an additional point at the middle of the path. The processor calculates a refitted curve using the additional point and the initial points identified in input step 158.

FIG. 2B illustrates an additional point 136 that the processor has added to the midpoint of a geodesic path between disconnected points 116A and 116F.

The processor samples points on the refitted curve, projects the points onto the mesh, and measures the distances between neighboring projected points. The processor uses the measured distances to evaluate the refitted curve, as described above for step 162, so as to decide if the refitted curve is open or closed.

The flowchart then returns to decision step 162, as shown by an arrow 176.

It will be understood that decision step 164, recomputing step 172, and arrow 176 illustrate an iterative process followed by processor 22 to achieve convergence, i.e. to generate a closed curve that may be used to segment anatomical portions 108 and 112.

FIG. 2B also illustrates a refitted curve 140, that the processor has evaluated as being a closed curve, and the processor may use curve 140 as a closed segmentation curve separating portions 108 and 112.

In some cases, even though a closed curve may be generated for a 3D mesh, the closed curve does not divide the mesh into two disjoint regions. An example of a 3D mesh where this is the case is when the mesh contains a topological hole, i.e., has a genus equal to or greater than 1, and the curve passes through the topological hole. Examples of the present disclosure address this problem, as is explained with reference to FIGS. 4 and 5 below.

Figure 4:
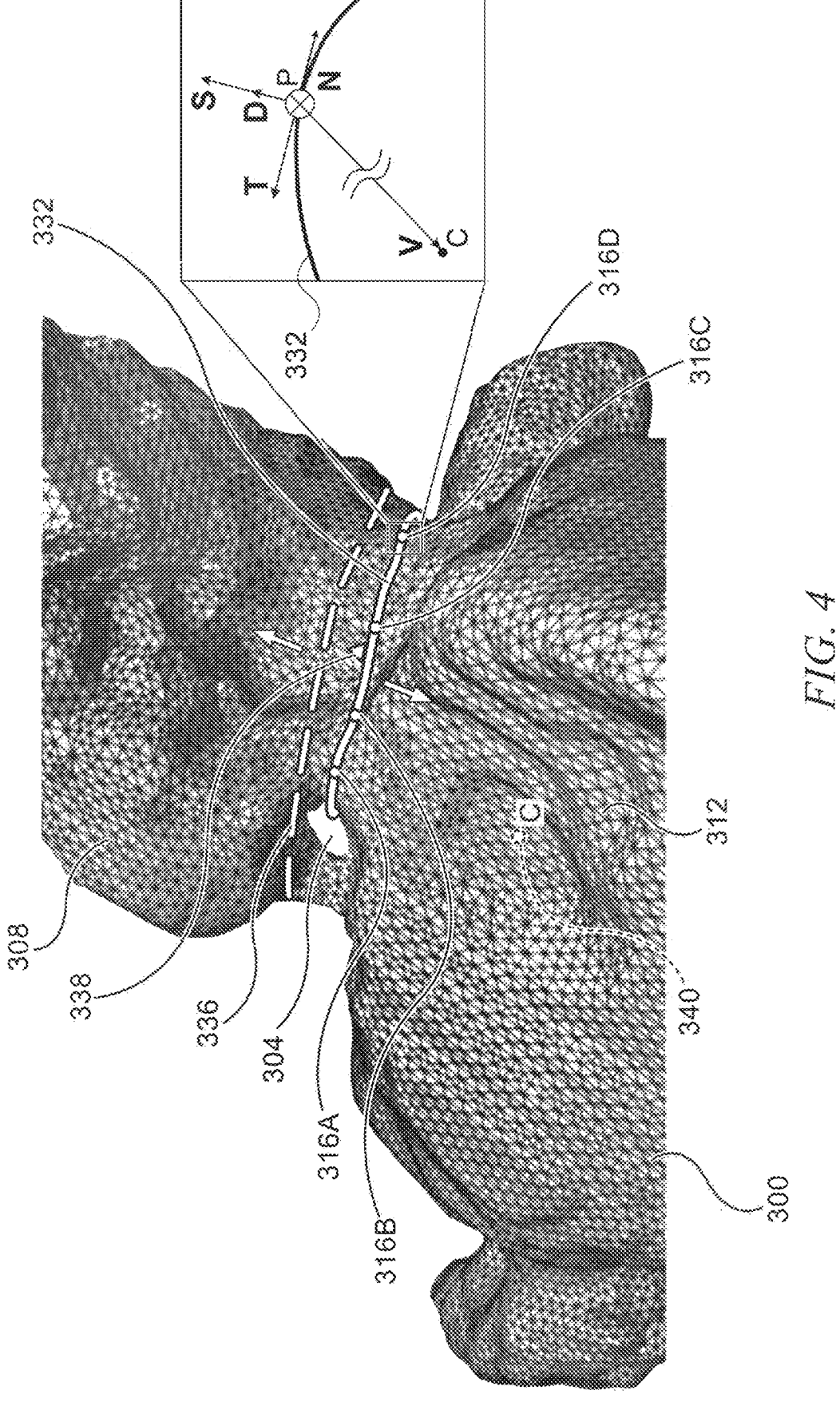
FIG. 4 is a schematic illustration of a mesh of a section of a heart, according to an example of the present disclosure.
Figure 5:
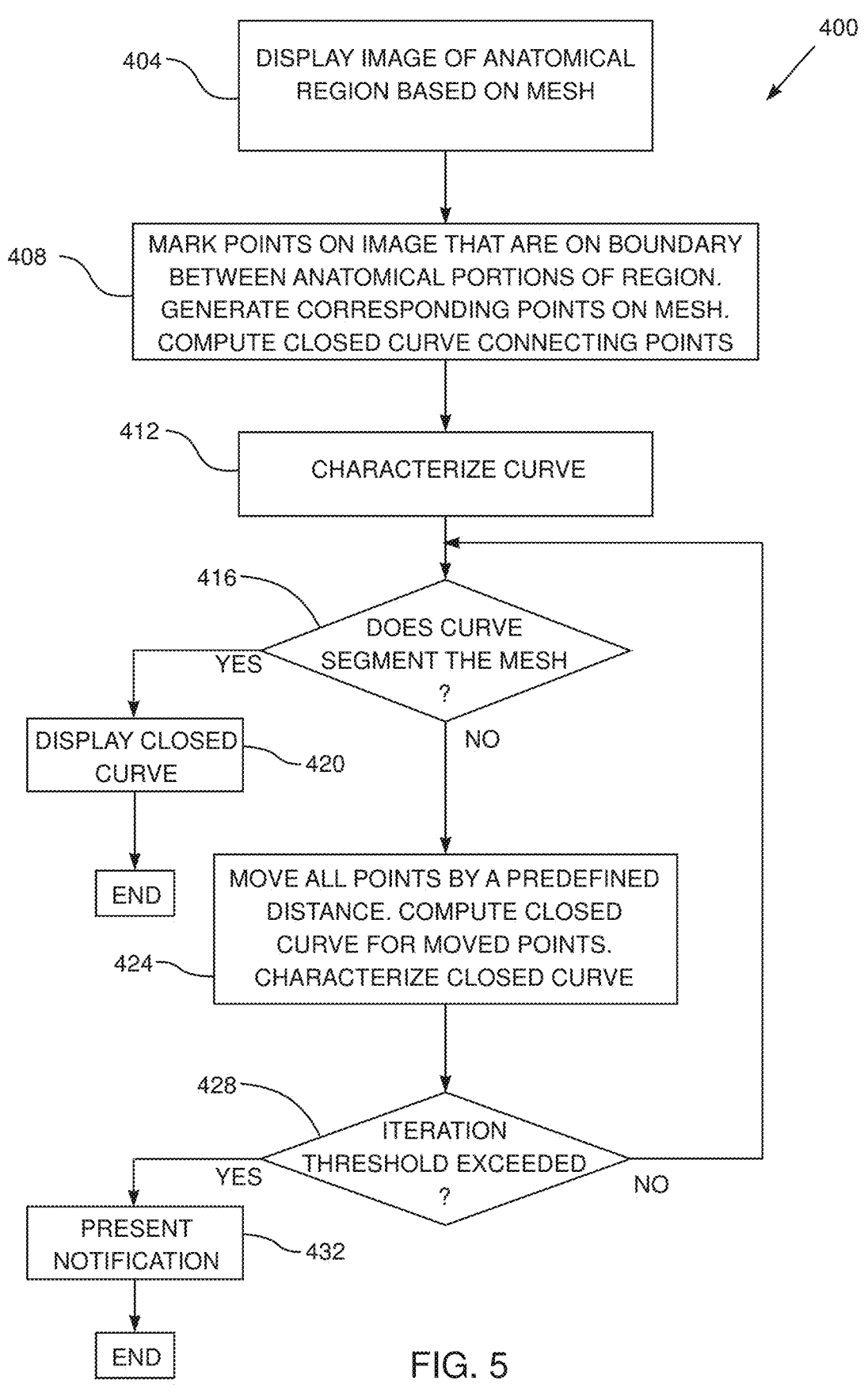
FIG. 5 is a flowchart of steps that are implemented to segment the mesh, according to an example of the present disclosure.

FIG. 4 is a schematic illustration of a 3D mesh 300 of a section of heart 12, as it may be presented to physician 24 on device 27, and FIG. 5 is a flowchart 400 of steps that are implemented to segment the mesh, according to an example of the present disclosure. Mesh 300 has a topological hole 304 in the mesh, and is assumed to be of a distal anatomical portion 308 and a proximal anatomical portion 312 of heart 12.

An initial step 404 of the flowchart is generally similar to initial step 154 of flowchart 150, so that an image of the section of the heart to be segmented is presented to physician 24 on display device 27. FIG. 4 illustrates the underlying mesh, mesh 300, and, as is the case for step 154, the mesh itself may be obtained by the processor computing mapping measurements made on the corresponding section of the heart by physician 24, as described above, or by any other convenient method.

In a user input step 408, physician 24 marks points, on the image of the section presented on device 27, that are assumed to be on a boundary dividing portion 308 from portion 312. The processor identifies corresponding points, herein assumed to comprise points 316A, 316B, 316C and 316D, generically referred to herein as points 316, and computes a closed curve 332 connecting the points. In one example the processor may use the algorithm represented by flowchart 150 to compute the closed curve, but other examples may use any other convenient method to determine the closed curve.

In a characterization step 412 the processor characterizes curve 332 by selecting a seed element of the mesh, herein assumed to be triangle 338 on one side of the curve 332, which may contact the curve. The processor then registers triangles of the mesh contacting the seed triangle, that do not cross curve 332, and iteratively repeats registering contacting triangles until all possible contacting triangles have been registered. The processor records the number of registered triangles, and continues to a decision step 416.

Decision step 416 determines if closed curve 332 corresponds to a boundary curve segmenting portion 308 and portion 312. If the number of triangles recorded in step 412 is a subset, i.e., is less than, the total number of triangles of mesh 300, then the subset of triangles populates one of portions 308 or 312. Consequently, closed curve 332 does segment the mesh, and is assumed to be the boundary curve segmenting portions 308 and 312. In this case the return of the decision step is positive.

However, if the number of triangles recorded in step 412 is equal to the total number of triangles of mesh 300, as is the case when closed curve 332 passes through topological hole 304, then the recorded triangles of step 412 populate the whole mesh. In this case the closed curve does not segment the mesh, and the return of decision step 416 is negative.

If decision step 416 returns positive, then in a presentation step 420 closed curve 332 is presented on device 27 to the physician as a segmentation curve for portions 308 and 312, and the flowchart ends.

If decision step 416 returns negative, control transfers to a modified curve step 424, wherein a closed curve 336, different from curve 332 is generated.

In step 424, each identified point 316, also referred to in a callout of FIG. 4 as point P, is moved by a predefined distance as described below, and closed curve 336 is generated from the new points, substantially as described for input step 408.

Movement of Point P

As shown in the callout of FIG. 4, processor 22 constructs a tangent vector T to curve 332 at point P, and a vector N normal to the mesh at point P. In the callout normal vector N is illustrated as a vector into the plane of the paper.

Processor 22 computes a cross-product of T and N, as shown by equation (1), to find a unitary direction vector D:

$$D=k_1(T\times N) \tag{1}$$

where $k_1$ is a constant that converts the cross-product to a unit vector pointing distally.

Point P is moved by a vector S, defined according to equation (2):

$$S=k_2D \tag{2}$$

where $k_2$ is a preset constant. In one example $k_2$ is selected so that the magnitude of the movement of P, its step ISI, is half the longest edge of the triangles of the mesh in the neighborhood of P.

In examples of the disclosure, P may be moved by its step distally or proximally.

To determine if movement of P is distal or proximal, a vector V from P to a central point C of mesh 300, also referred to herein as point 340, is calculated. Processor 22 calculates the dot-product V·D, and uses the dot-product to set the movement of P, as shown by conditions (3):

> If $V \cdot D < 0$, then $P$ is moved according to the direction given by $D$, i.e., distally.
>
> If $V \cdot D > 0$, then $P$ is moved according to the direction given by $-D$, i.e., proximally. (3)

It will be understood that at any given iteration, all points 316 move in one direction by a given step, either distally or proximally, so that curve 332 also moves distally or proximally, as illustrated by the arrows overlaid on mesh 300.

Once all points 316 have been moved, a closed curve is computed for the moved points and the curve is characterized, substantially as described above for steps 408 and 412.

Control from modified curve step 424 returns reiteratively, via an iteration count decision step 428, to decision step 416.

In examples of the present disclosure, processor 22 is configured to count the number of iterations performed by step 424, and in one example a threshold of three distal iterations and three proximal iterations for the movement of points 316 is set. In a disclosed example the distal iterations are performed first, and, if these do not lead to decision step 416 returning positive, the proximal iterations are performed.

Decision step 428 checks if the iteration threshold is exceeded, which may be the case, for example, if the mesh geometry is complex. In this event decision step 428 returns positive, and in a report step 432, physician 24 may be notified that automatic segmentation of portions 308 and 312 has not been achieved, and the flowchart ends.

if the threshold is not exceeded, in which case decision step 428 returns negative, the flowchart returns to decision step 416, and the reiterations continue.

In examples of the disclosure the algorithms illustrated by flowcharts 150 and 400, and their accompanying descriptions may be performed sequentially. Alternatively, each of the algorithms may be performed separately, independent of the other algorithm.

EXAMPLES

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system includes a display and a processor. The processor is configured to obtain a three-dimensional mesh representing a first anatomical portion and a second anatomical portion, which is connected to the first anatomical portion, to receive, from a user, an input indicating multiple points corresponding to a boundary between the first anatomical portion and the second anatomical portion, to fit a curve to the points and to project the curve onto the mesh, and to perform an iterative process, subsequently to projecting the curve onto the mesh and in response to the curve not being closed, until the curve is closed. Each iteration of the process includes adding, to the points, another point lying on the mesh between endpoints of the curve, and subsequently to adding the other point, refitting the curve to the points. The processor is further configured to display the mesh on the display, based on the curve, so as to demarcate the first anatomical portion from the second anatomical portion.

Example 2

The system according to Example 1, wherein the processor is configured to project the curve onto the mesh by adding, to the points, multiple interpolated points lying on the curve, and subsequently to adding the interpolated points, projecting each of the points onto the mesh.

Example 3

The system according to any one of Examples 1-2, wherein the processor is configured to obtain the mesh by computing the mesh.

Example 4

The system according to any one of Examples 1-3, wherein the processor is configured to fit the curve using a B-spline.

Example 5

The system according to any one of Examples 1-4, wherein adding the other point includes computing a path of minimal geodesic distance passing between the endpoints on the mesh, and adding the other point at a midpoint of the path.

Example 6

The system according to any one of Examples 1-5, wherein the first anatomical portion includes a left atrium body of a heart, and wherein the second anatomical portion includes a pulmonary vein.

Example 7

A method includes obtaining a three-dimensional mesh representing a first anatomical portion and a second anatomical portion, which is connected to the first anatomical portion. The method further includes receiving, from a user, an input indicating multiple points corresponding to a boundary between the first anatomical portion and the second anatomical portion. The method further includes fitting a curve to the points and projecting the curve onto the mesh. The method further includes, subsequently to projecting the curve onto the mesh, in response to the curve not being closed, performing an iterative process until the curve is closed. Each iteration of the process includes adding, to the points, another point lying on the mesh between endpoints of the curve, and subsequently to adding the other point, refitting the curve to the points.

Example 8

The method according to Example 7, wherein projecting the curve onto the mesh includes adding, to the points, multiple interpolated points lying on the curve, and subsequently to adding the interpolated points, projecting each of the points onto the mesh.

Example 9

The method according to any one of Examples 7-8, wherein obtaining the mesh comprises obtaining the mesh by computing the mesh.

Example 10

The method according to any one of Examples 7-9, wherein fitting the curve comprises fitting the curve using a B-spline.

Example 11

The method according to any one of Examples 7-10, wherein adding the other point includes computing a path of minimal geodesic distance passing between the endpoints on the mesh, and adding the other point at a midpoint of the path.

Example 12

The method according to any one of Examples 7-11, wherein the first anatomical portion includes a left atrium body of a heart, and wherein the second anatomical portion includes a pulmonary vein.

Example 13

A system includes a display and a processor. The processor is configured to obtain a three-dimensional mesh representing a first anatomical portion and a second anatomical portion, which is connected to the first anatomical portion, to receive, from a user, an input indicating a boundary between the first anatomical portion and the second anatomical portion, to fit a closed curve to multiple points on the mesh based on the input, and to perform an iterative process, in response to the curve not segmenting the mesh into two separate parts, until the curve segments the mesh into two separate parts. Each iteration of the process includes moving each point of the points to another location on the mesh, and subsequently to moving each point, refitting the curve to the points. The processor is further configured to display the mesh on the display, based on the curve, so as to demarcate the first anatomical portion from the second anatomical portion.

Example 14

The system according to Example 13, wherein moving each point includes computing a tangent vector to the curve, and a normal vector to the mesh, at the point, computing a direction vector from a cross-product of the tangent vector and the normal vector, and moving the point in a direction of the direction vector.

Example 15

The system according to Example 14, wherein computing the direction vector includes computing a pointing vector, which points from a center of the mesh to the point, computing components of the direction vector as components of the cross-product, and computing a sign of the direction vector such that a dot-product of the pointing vector and the direction vector has a predefined sign.

Example 16

The system according to any one of Examples 14-15, wherein moving the point includes moving the point by the direction vector scaled by a predefined step size.

Example 17

The system according to Example 16, wherein the mesh is a triangular mesh including multiple edges, and wherein the predefined step size is half of a largest one of the edges within a neighborhood of the curve.

Example 18

The system according to any one of Examples 16-17, wherein the direction vector is a unit vector.

Example 19

The system according to any one of Examples 13-18, wherein the first anatomical portion includes a left atrium body of a heart, and wherein the second anatomical portion includes a pulmonary vein.

Example 20

The system according to Example 13, and comprising, in response to fitting the closed curve, characterizing the curve by selecting a seed element of the mesh, and iteratively registering and enumerating further elements of the mesh contacting the seed element.

Example 21

A method includes obtaining a three-dimensional mesh representing a first anatomical portion and a second anatomical portion, which is connected to the first anatomical portion. The method further includes receiving, from a user, an input indicating a boundary between the first anatomical portion and the second anatomical portion. The method further includes, based on the input, fitting a closed curve to multiple points on the mesh. The method further includes, in response to the curve not segmenting the mesh into two separate parts, performing an iterative process until the curve segments the mesh into two separate parts. Each iteration of the process includes moving each point of the points to another location on the mesh, and subsequently to moving each point, refitting the curve to the points.

Example 22

The method according to Example 21, wherein moving each point comprises computing a tangent vector to the curve, and a normal vector to the mesh, at the point, computing a direction vector from a cross-product of the tangent vector and the normal vector, and moving the point in a direction of the direction vector.

Example 23

The method according to Example 22, wherein computing the direction vector comprises computing a pointing vector, which points from a center of the mesh to the point, computing components of the direction vector as components of the cross-product, and computing a sign of the direction vector such that a dot-product of the pointing vector and the direction vector has a predefined sign.

Example 24

The method according to any one of Examples 22-23, wherein moving the point comprises moving the point by the direction vector scaled by a predefined step size.

Example 25

The method according to Example 24, wherein the mesh is a triangular mesh including multiple edges, and wherein the predefined step size is half of a largest one of the edges within a neighborhood of the curve.

Example 26

The method according to any one of Examples 24-25, wherein the direction vector is a unit vector.

Example 27

The method according to any one of Examples 21-26, wherein the first anatomical portion includes a left atrium body of a heart, and wherein the second anatomical portion includes a pulmonary vein.

Example 28

The method according to example 21, and comprising, in response to fitting the closed curve, characterizing the curve by selecting a seed element of the mesh, and iteratively registering and enumerating further elements of the mesh contacting the seed element.

It will be appreciated by persons skilled in the art that the present disclosure is not limited to what has been particularly shown and described hereinabove. Rather, the scope of the present disclosure includes both combinations and sub-combinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a display; and
a processor, configured to:
   obtain a three-dimensional mesh representing a first anatomical portion and a second anatomical portion, which is connected to the first anatomical portion,
   receive, from a user, an input indicating multiple points corresponding to a boundary between the first anatomical portion and the second anatomical portion,
   fit a curve to the points and project the curve onto the mesh,
   subsequently to projecting the curve onto the mesh, in response to the curve not being closed, perform an iterative process without receiving additional user input until the curve is closed, each iteration of the process including:
      computing a path of minimal geodesic distance passing between endpoints of a curve on the mesh, wherein each of the endpoints is a disconnected point terminating the curve,
      adding, to the points, another point lying on the mesh between the endpoints of the curve, wherein the other point is added at a midpoint of the path outside of the curve, and
      subsequently to adding the other point, refitting the curve to the points, and
   based on the curve, display the mesh on the display so as to demarcate the first anatomical portion from the second anatomical portion.

2. The system according to claim 1, wherein the processor is configured to project the curve onto the mesh by:

adding, to the points, multiple interpolated points lying on the curve, and subsequently to adding the interpolated points, projecting each of the points onto the mesh.

3. The system according to any one of claims 1-2, wherein the processor is configured to obtain the mesh by computing the mesh.

4. The system according to claim 1, wherein the processor is configured to fit the curve using a B-spline.

5. The system according to claim 1, wherein the first anatomical portion includes a left atrium body of a heart, and wherein the second anatomical portion includes a pulmonary vein.

6. A method, comprising:

obtaining a three-dimensional mesh representing a first anatomical portion and a second anatomical portion, which is connected to the first anatomical portion;

receiving, from a user, an input indicating multiple points corresponding to a boundary between the first anatomical portion and the second anatomical portion;

fitting a curve to the points and projecting the curve onto the mesh;

subsequently to projecting the curve onto the mesh, in response to the curve not being closed, performing an iterative process without receiving additional user input until the curve is closed, each iteration of the process including:

computing a path of minimal geodesic distance passing between endpoints of a curve on the mesh, wherein each of the endpoints is a disconnected point terminating the curve, adding, to the points, another point lying on the mesh between the endpoints of the curve, wherein the other point is added at a midpoint of the path outside of the curve, and subsequently to adding the other point, refitting the curve to the points.

7. The method according to claim 6, wherein projecting the curve onto the mesh comprises:

adding, to the points, multiple interpolated points lying on the curve; and subsequently to adding the interpolated points, projecting each of the points onto the mesh.

8. The method according to any one of claims 6-7, wherein obtaining the mesh comprises obtaining the mesh by computing the mesh.

9. The method according to claim 6, wherein fitting the curve comprises fitting the curve using a B-spline.

10. The method according to claim 6, wherein the first anatomical portion includes a left atrium body of a heart, and wherein the second anatomical portion includes a pulmonary vein.

11. A system, comprising:

a display; and a processor, configured to:

obtain a three-dimensional mesh representing a first anatomical portion and a second anatomical portion, which is connected to the first anatomical portion, receive, from a user, an input indicating a boundary between the first anatomical portion and the second anatomical portion, based on the input, fit a closed curve to multiple points on the mesh, in response to the curve not segmenting the mesh into two separate parts, perform an iterative process without receiving additional user input until the curve segments the mesh into two separate parts, each iteration of the process including:

moving each point of the points to another location on the mesh, and subsequently to moving each point, refitting the curve to the points, and based on the curve, display the mesh on the display so as to demarcate the first anatomical portion from the second anatomical portion.

12. The system according to claim 11, wherein moving each point includes:

computing a tangent vector to the curve, and a normal vector to the mesh, at the point, computing a direction vector from a cross-product of the tangent vector and the normal vector, and moving the point in a direction of the direction vector.

13. The system according to claim 12, wherein computing the direction vector includes:

computing a pointing vector, which points from a center of the mesh to the point, computing components of the direction vector as components of the cross-product, and computing a sign of the direction vector such that a dot-product of the pointing vector and the direction vector has a predefined sign.

14. The system according to any one of claims 12-13, wherein moving the point includes moving the point by the direction vector scaled by a predefined step size.

15. The system according to claim 14, wherein the mesh is a triangular mesh including multiple edges, and wherein the predefined step size is half of a largest one of the edges within a neighborhood of the curve.

16. The system according to claim 14, wherein the direction vector is a unit vector.

17. The system according to claim 11, wherein the first anatomical portion includes a left atrium body of a heart, and wherein the second anatomical portion includes a pulmonary vein.

18. The system according to claim 11, comprising, in response to fitting the closed curve, characterizing the curve by selecting a seed element of the mesh, and iteratively registering and enumerating further elements of the mesh contacting the seed element.

19. A method, comprising:

obtaining a three-dimensional mesh representing a first anatomical portion and a second anatomical portion, which is connected to the first anatomical portion;

receiving, from a user, an input indicating a boundary between the first anatomical portion and the second anatomical portion;

based on the input, fitting a closed curve to multiple points on the mesh; and in response to the curve not segmenting the mesh into two separate parts, performing an iterative process without receiving additional user input until the curve segments the mesh into two separate parts, each iteration of the process including:

moving each point of the points to another location on the mesh, and subsequently to moving each point, refitting the curve to the points.

20. The method according to claim 19, wherein moving each point comprises:

computing a tangent vector to the curve, and a normal vector to the mesh, at the point;

computing a direction vector from a cross-product of the tangent vector and the normal vector; and moving the point in a direction of the direction vector.

21. The method according to claim 20, wherein computing the direction vector comprises:

computing a pointing vector, which points from a center of the mesh to the point;

computing components of the direction vector as components of the cross-product; and computing a sign of the direction vector such that a dot-product of the pointing vector and the direction vector has a predefined sign.

22. The method according to any one of claims 20-21, wherein moving the point comprises moving the point by the direction vector scaled by a predefined step size.

23. The method according to claim 22, wherein the mesh is a triangular mesh including multiple edges, and wherein the predefined step size is half of a largest one of the edges within a neighborhood of the curve.

24. The method according to claim 22, wherein the direction vector is a unit vector.

25. The method according to claim 19, wherein the first anatomical portion includes a left atrium body of a heart, and wherein the second anatomical portion includes a pulmonary vein.

26. The method according to claim 19, comprising, in response to fitting the closed curve, characterizing the curve by selecting a seed element of the mesh, and iteratively registering and enumerating further elements of the mesh contacting the seed element.

* * * * *